United States Patent [19]

Hardtmann

[11] 3,982,000

[45] Sept. 21, 1976

[54] ALKYL-SUBSTITUTED-TRICYCLIC QUINAZOLINONES AS BRONCHODILATORS

[75] Inventor: Goetz E. Hardtmann, Florham Park, N.J.

[73] Assignee: Sandoz, Inc., E. Hanover, N.J.

[22] Filed: Feb. 21, 1975

[21] Appl. No.: 551,734

Related U.S. Application Data

[60] Division of Ser. No. 325,081, Jan. 19, 1973, Pat. No. 3,905,976, which is a continuation-in-part of Ser. No. 201,982, Nov. 24, 1971, abandoned.

[52] U.S. Cl. .......................... 424/251; 260/256.4 F
[51] Int. Cl.² ...................................... A61K 31/505
[58] Field of Search ............. 260/256.4 F; 424/251

[56] References Cited
UNITED STATES PATENTS

| | | |
|---|---|---|
| 3,598,823 | 8/1971 | Hardtmann.................. 260/256.4 F |
| 3,790,573 | 2/1974 | Blackburn et al............ 260/256.4 F |
| 3,905,976 | 9/1975 | Hardtmann.................. 260/256.4 F |

*Primary Examiner*—Nicholas S. Rizzo
*Assistant Examiner*—James H. Turnipseed
*Attorney, Agent, or Firm*—Gerald D. Sharkin; Richard E. Vila

[57] ABSTRACT

The compounds are alkyl-substituted-tricyclic quinazolinones of the class of imidazo[2,1-b]quinazolin-5-ones and pyrimido[2,1-b]quinazolin-6-one, e.g., 2-methyl-2,3-dihydro-10-(4'-fluorobenzyl)-imidazo[2,1-b]quinazolin-5(1OH)-one, useful, for example, as bronchodilator agents. Processes for preparation of said compounds include the reaction of a N-carboxy anthranilic anhydride (an isatoic anhydride) with an alkyl substituted cyclic pseudothiourea such as a 2-organomercapto-4,5-dihydroimidazole or a 2-organomercapto-3,4,5,6-tetrahydropyrimidine and the cyclization of a 2-(ω-hydroxy(branched) alkylamino)-4-quinazolone.

11 Claims, No Drawings

ALKYL-SUBSTITUTED-TRICYCLIC QUINAZOLINONES AS BRONCHODILATORS

This application is a division of application Ser. No. 325,081, filed Jan. 19, 1973, now U.S. Letters Pat. No. 3,905,976, which is a continuation-in-part of abandoned application Ser. No. 201,982, filed Nov. 24, 1971.

The present invention relates to tricyclic compounds which are quinazolinones, and to their preparation. The invention also relates to pharmaceutical methods and compositions for utilization of the compounds based on their biological activity.

The present invention provides compounds of the formula I:

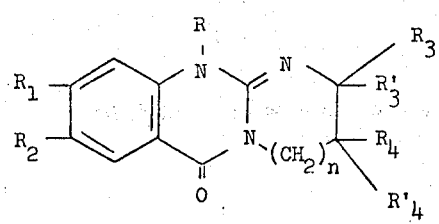

wherein each of $R_1$ and $R_2$ is, independently, hydrogen, halo of atomic weight not greater than 36 or lower alkyl of 1 to 3 carbon atoms, or are either both hydroxy or both lower alkoxy of 1 to 2 carbon atoms; or one is hydrogen and the other bromo, hydroxy or lower alkoxy of 1 to 2 carbon atoms;

$n$ is 0 or 1;

each of $R_3$, $R_3'$, $R_4$ and $R_4'$ is hydrogen or lower alkyl of 1 to 3 carbons provided that at least one but not more than three of $R_3$, $R_3'$, $R_4$ and $R_4'$ is lower alkyl;

R is lower alkyl of 1 to 5 carbon atoms,

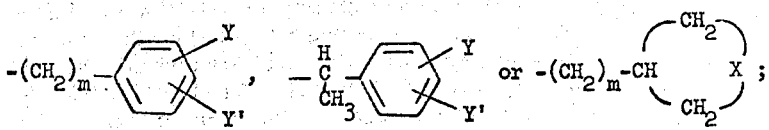

X is a direct bond or $-(CH_2)_y-$ y is 1 to 3, m is 0 to 2;

each of Y and Y' is, independently, hydrogen, halo of atomic weight not greater than 36, i.e. fluoro or chloro, or lower alkyl of 1 to 3 carbon atoms, or either both are hydroxy or both are lower alkoxy of 1 to 2 carbon atoms, or one is hydrogen and the other bromo, hydroxy or lower alkoxy of 1 to 2 carbon atoms, provided that no more than two of $R_1$, $R_2$, Y and Y' are hydroxy, further provided that neither of $R_1$ and $R_2$ is hydroxy when either of Y and Y' is alkoxy and still further provided that neither of Y and Y' is hydroxy when either of $R_1$ and $R_2$ is alkoxy, or a pharmaceutically acceptable acid addition salt thereof.

The one method for preparation of compounds of formula I involves reacting in a Step A a compound of the formula II:

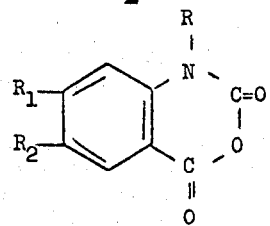

wherein $R_1$, $R_2$ and R are as defined, with a compound of formula III:

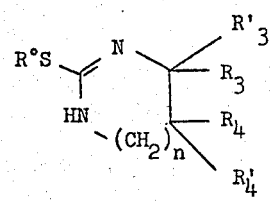

wherein $n$, $R_3$, $R_3'$, $R_4$ and $R_4'$ are as defined and $R°$ is lower alkyl or benzyl.

The preparation of compounds I by Step A can be carried out at temperatures in the range of 20°C. to 160°C., more usually 20°C. to 140°C., preferably 80°C. to 120°C. The reaction is conveniently carried out in an organic solvent of conventional type providing an inert medium. The aromatic solvents and cyclic ethers suitable for use at reflux temperatures represent the preferred solvents, e.g. toluene and dioxane. The reaction is preferably carried out in the presence of a base, e.g. sodium hydroxide or sodium carbonate; and when the compound III is employed in acid addition salt form, it is of course desirable to employ an amount of base somewhat greater than the amount necessary to neutralize the acid. The reaction product of formula I may be recovered from the reaction of Step A by working up by conventional procedures.

The compounds of formula I other than those bearing a hydroxy substituent are preferably prepared by reacting in a Step B a compound of the formula IV:

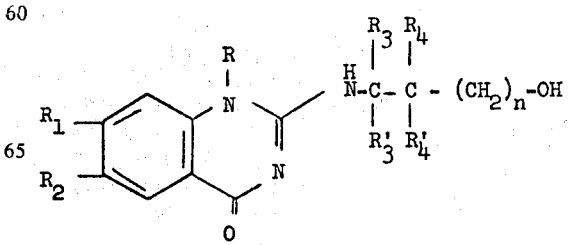

in which R, $R_1$, $R_2$, $R_3$, $R_3'$, $R_4$, $R_4'$ and $n$ are as above-defined, with a cyclizing agent, and treating the reaction product with an acid binding agent.

The preparation of compounds I from compounds IV involves a cyclization of known type carried out by treating a compound IV with a reagent suitable for such type of cyclization, for example, a phosphorus halide or thionyl halide in which the halide has an atomic weight of from 35 to 80, i.e. the chloride or bromide, more preferably the chloride. The preferred reagent is thionyl chloride. The reaction with the cyclizing reagent may be carried out in absence of a solvent or in the presence of inert solvents of known type, e.g. the halogen-containing hydrocarbons such as methylene chloride and chloroform, and the aromatic solvents such as benzene and pyridine. An excess of the cyclizing agent may, however, where appropriate, be employed to provide a solvent. The treatment with an acid-binding agent, e.g., an inorganic base or tertiary amine, is preferably effected after removal of the remaining cyclizing reagent. The reaction product of formula I may be isolated from the reaction mixture by working up by established procedures.

The compounds of the formula I bearing a hydroxy substituent, i.e. one or more of $R_1$, $R_2$, Y and Y' is hydroxy, are most preferably prepared in a Step C reaction by hydrolysis of the corresponding alkoxy substituted compound of the formula I. The hydrolysis of Step C may be carried out in a conventional manner employing the usual conditions generally utilized for converting an alkoxy group to a hydroxy group, e.g. by treatment of said alkoxy compound of the formula I with aqueous hydrobromic acid at elevated temperatures, e.g., 40°C. to 150°C.

The compounds of the formulae II and III employed as starting materials in the reaction of Step A are either known or may be prepared from known materials by established procedures.

The compounds of formula IV may be prepared by reacting a compound of the formula V:

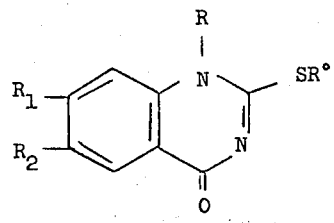

V wherein R°, R, $R_1$ and $R_2$ are as defined, with a compound of formula VI:

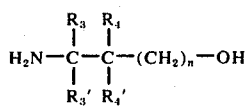

VI wherein $n$, $R_3$, $R_3'$, $R_4$ and $R_4'$ are as defined.

The preparation of the compounds IV from compounds V and VI is suitably carried out at temperature in the range of from 0°C. to 120°C., preferably 20°C. to 80°C. An excess of compound VI is preferably employed. The reaction may be carried out in the absence of a solvent but is preferably conducted in the presence of an inert organic solvent which may be any of several of the well known types, preferably a chlorine-containing hydrocarbon such as chloroform and methylene chloride. The reaction product of formula IV may be isolated from the reaction mixture for use in preparation of compounds I by working up by established procedures.

The compounds of formula V may be prepared by reacting a compound of formula VII:

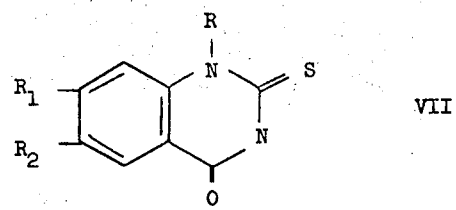

VII wherein R, $R_1$ and $R_2$ are as defined, with an iodo compound of formula VIII:

VIII wherein R° is as defined.

The preparation of compounds V by reacting of compounds VI and VIII is suitably carried out at temperatures in the range of from 0°C. to 100°C., preferably 15°C. to 60°C. The reaction is desirably effected in the presence of an inert organic solvent which may be any of several well known types, preferably a lower alcohol of 1 to 5 carbon atoms or an ether, e.g., ethanol and dioxane, preferably ethanol. The reaction product of formula V may be isolated from the reaction mixture for use in preparation of compounds IV by working up by established procedures.

The compounds of the formulae VI, VII and VIII are either known or may be prepared from known materials by established procedures.

Also within the scope of the novel compounds provided by the invention are pharmaceutically acceptable salts not materially depreciating the pharmacological effect of the compounds. Such salts include the acid addition salts of known type, e.g. the hydrochloride. The acid addition salts may be produced from the corresponding free bases by conventional procedures. Conversely, the free bases may be obtained from the salts by procedures known in the art.

The compounds of formula I of the invention are useful because they possess biological activity. In particular, the compounds of the formula I in which R is alkyl or a phenyl or substituted phenyl ring separated from the ring nitrogen by an alkylene moiety, i.e. the compounds of the following formulae Ia, Ib and Ic:

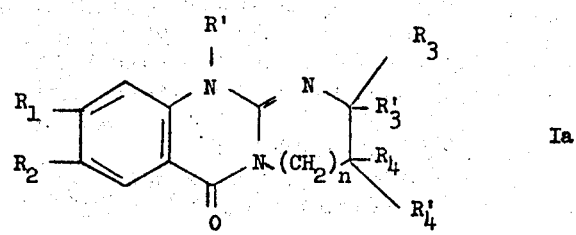

Ia

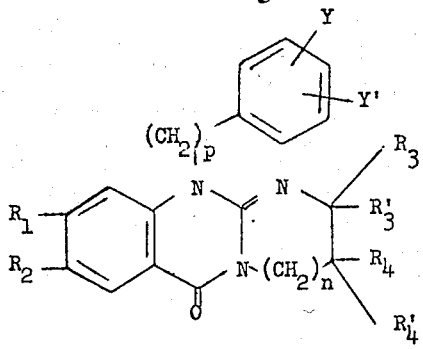

Ib

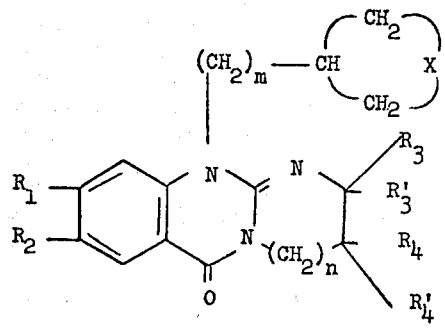

Ic

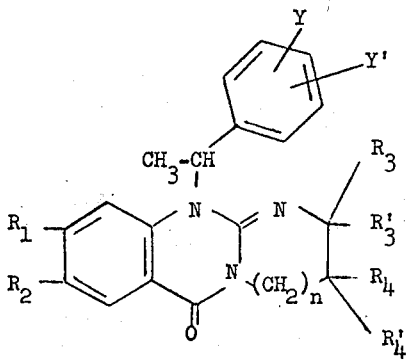

which $R_1$, $R_2$, Y, Y', $R_3$, $R_3'$, $R_4$, $R_4'$ and n are as defined and p is 1 or 2 and R' is alkyl of 1 to 5 carbon atoms are useful as bronchodilator agents as indicated by measuring bronchial resistance on intravenous administration (0.1 – 5 mgs./kgs.) in the anesthetized guinea pig and according to the test of Knozett and Rossler, Arch. Exp. Path. and Pharmak. 195:71 (1940); and by observing the respiratory status on oral administration (0.5 – 100 mgs./kgs.) to the unanesthetized guinea pig exposed to aerosolized histamine dihydrochloride according to a modification of the method of Van Arman et al., J. Pharm. pharmacol. Exptl. Therap. 133:90–97, 1961; and in vitro by observing the effect (0.1 – 30 micrograms/ml.) on strips of guinea pig trachea according to the method of Constantine, J. Pharm. Pharmacol. 17: 384–385, 1960. For such use and depending upon known variables satisfactory results are obtained in general on the daily administration of from 0.5 to 100 milligrams per kilogram of body weight, preferably given in divided doses 2 to 4 times a day, or in sustained release form. For most mammals the administration of from 30 to 3000 milligrams per day provides satisfactory results and dosage forms suitable for internal administration comprise 8 to 1500 milligrams of the compound in admixture with a solid or liquid pharmaceutical carrier or diluent.

The compounds of the formula I in which R is phenyl or substituted phenyl or cycloalkyl or cycloalkylalkyl, i.e. the compound of the following formulae Id and Id:

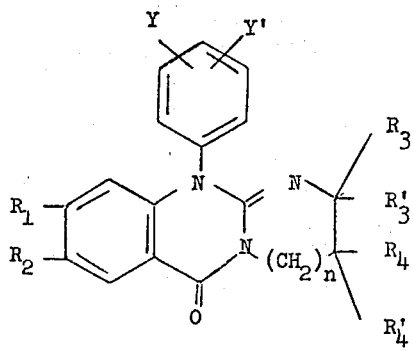

Id wherein $R_1$, $R_2$, Y, Y', X, $R_3$, $R_3'$, $R_4$, $R_4'$, m and n are as defined, are also useful as hypotensive/anti-hypertensive agents as indicated by a lowering of blood pressure on intravenous administration to the anesthetized dog. For such use and depending upon known variables satisfactory results are obtained in general on daily administration of from 0.1 to 100 milligrams per kilogram of body weight. For most mammals the administration of from 40 to 1500 milligrams per day provides satisfactory results and dosage forms for internal administration comprise from 10 to 750 milligrams in combination with a suitable carrier. The preferred compounds for effecting a lowering of blood pressure are those in which R is cycloalkylalkyl, n is 0 and $R_1$ and $R_2$ are hydrogen, more preferably R is cyclopropylmethyl.

The preferred compounds of the invention from the standpoint of bronchodilator activity, e.g. in the histamine aerosol assay, are those in which R is benzyl including substituted benzyl, particularly unsubstituted benzyl and more particularly those which have a 4-halo substituted-benzyl, and the more preferred such compounds are those in which each of $R_1$ and $R_2$ is hydrogen, and those in which n is 0.

For the uses indicated above, the compounds may be combined with a pharmaceutically acceptable carrier, and such other conventional adjuvants as may be necessary, and administered orally or parenterally. For most uses oral administration with carriers is preferred and may take place in such conventional forms as tablets, dispersible powders granules, capsules, suspensions, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents(methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g. calcium carbonate, calcium phosphate and kaolin. The preferred pharmaceutical compositions from the standpoint of preparation and ease of oral administration are solid compositions, particularly hard-filled capsules and tablets. Parenteral administration may be in such conventional forms as injectionable solutions and suspensions.

A representative formulation is a tablet for oral administration 2 to 4 times a day for effecting a reduction in blood pressure and prepared by conventional tabletting techniques to contain the following ingredients:

| Ingredients | Weight (mg.) |
|---|---|
| 10-cyclopropylmethyl-2,3-dihydro-2,2-dimethyl-imidazo[2,1-b]quinazolin-5(10H)-one | 25 |
| Tragacanth | 10 |
| Lactose | 222.5 |
| Corn Starch | 25 |
| Talcum | 15 |
| Magnesium Stearate | 2.5 |

A representative formulation is also a capsule for oral administration 2 to 4 times a day for effecting a reduction in blood pressure and prepared by conventional capsulating techniques to contain the following ingredients:

| Capsule Ingredients | Weight (Mg.) |
|---|---|
| 10-cyclopropylmethyl-2,3-dihydro-2-methyl-imidazo[2,1-b]quinazolin-5(10H)-one | 25 |
| Lactose | 316 |
| Sterotex K (a triglycerol ester lubricant) | 10 |

Compounds of the invention of particular interest are also those in which $R_3$ and $R_3'$ are both alkyl with the $R_4$ being hydrogen or alkyl, preferably hydrogen and those in which $R_4$ and $R_4'$ are both alkyl with the $R_3$ being hydrogen or alkyl, preferably hydrogen, and more particularly with $n$ being 0. In such compounds $R_3$, $R_3'$, $R_4$ and $R_4'$ are preferably methyl and/or ethyl, more preferably methyl.

A representative formulation is a tablet for oral administration 2 to 4 times a day for prophylatic treatment of bronchial asthma and prepared by conventional tabletting techniques to contain the following ingredients:

| Ingredients | Weight (mg.) |
|---|---|
| 10-(4'-fluorobenzyl)-2,2-dimethyl-2,3-dihydro-imidazo[2,1-b]quinazolin-5(10H)-one | 25 |
| Tragacanth | 10 |
| Lactose | 222.5 |
| Corn Starch | 25 |
| Talcum | 15 |
| Magnesium Stearate | 2.5 |

In addition, the compounds of the formula I may be administered as bronchodilators by inhalation therapy in a conventional manner, e.g., by the use of nebulizers, vaporizers, aerosols and the like. Compositions for use in administration by inhalation therapy may be prepared according to conventional procedures and contain the usual conventional ingredients employed in such compositions. A representative aerosol formulation prepared by conventional techniques for use with a metered value system contains the following ingredients:

| | |
|---|---|
| 10-(4'-fluorobenzyl)-3-methyl-2,3-dihydro-imidazo[2,1-b]quinazolin-5(10H)-one | 0.4–20% |
| Ethyl alcohol | 10–40% |
| Ascorbic Acid | 1–10% |
| Freon 11 | 10–30% |
| Freon 114 | 10–30% |
| Freon 12 | 30–60% |
| Buffer System - pH control | q.s. |
| Flavor | q.s. |

The following examples show representative compounds encompassed within the scope of this invention and the manner in which such compounds are prepared. However, it is to be understood that the examples are for purposes of illustration only.

EXAMPLE 1

7-Chloro-2,3-dihydro-2,10-dimethyl-imidazo [2,1-b] quinazolin-5 (10H)-one

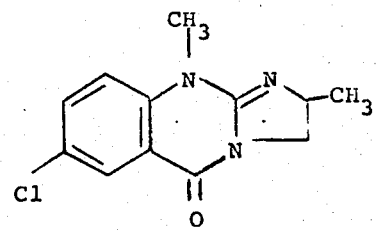

Step a. Preparation of 6-Chloro-1-methyl-2-methyl-mercapto-4-quinazolinone

A mixture of 35 g. of 6-chloro-1-methyl-2-thioquinazoline-2,4-dione, 500ml. ethanol and 50 g. of methyl iodide is stirred at room temperature for 48 hour. The ethanol is evaporated off in vacuo to obtain a crude oil of 6-chloro-1-methyl-2-methylmercapto-4-quinazolinone.

Step b. Preparation of 6-Chloro-1-methyl-2-(2-hydroxypropylamino)-4-quinazolone 30 g. of the crude material obtained in step a is added to a solution of 72 g. of 2-hydroxy-propylamine in 300 ml of chloroform. The mixture is stirred at 30°C. for 2 hours and then ½ hour at 65°C. The solvent is evaporated and the residue titurated with ice and water (~400 ml). This mixture is extracted 3 times with 200 ml ethyl acetate / Benzene (3:1). The combined organic solutions are extracted with water until the aqueous extract is neutral. After drying ($Na_2SO_4$) the solvent was evaporated in vacuo to obtain 6-Chloro-1-methyl-2-(2-hydroxypropylamino)-4-quinazolone.

Step c. Preparation of 7-Chloro-2,3-dihydro-2,10-dimethyl-imidazo [2,1-b] quinazolin-5(10H)-one The product obtained in step b in the amount of 28 g. is combined with 100 ml of thionyl chloride and the mixture heated to 80°C. for 3 hours. The resulting mixture is evaporated in vacuo and the residue dissolved in 300 ml of chloroform followed by washing once with 100 ml of 2N sodium hydroxide solution and three times with saturated sodium chloride solution. After drying (Na$_2$SO$_4$) the solvent is evaporated in vacuo and the residue chromatographed on silica gel using methylene chloride as the solvent. The head fractions which are eluted yield 7-chloro-2,3-dihydro-2,10-dimethyl-imidazo[2,1-b] quinazolin-5(10H)-one.

EXAMPLE 2

Following the procedure of Example 1, the following compounds of the invention are prepared:
- A. 2,3,11-trimethyl-8-chloro-2,3,4,11-tetrahydro-pyrimido[2,1-b]quinazolin-6-one.
- B. 2-methyl-2,3-dihydro-10-benzyl-imidazo[2,1-b]quinazolin-5(10H)-one.
- C. 2-methyl-2,3-dihydro-10-(4'-fluorobenzyl)-imidazo[2,1-b]quinazolin-5(10H)-one, m.p. 122°-125°C.
- D. 3-methyl-2,3-dihydro-10-benzyl-imidazo[2,1-b]quinazolin-5(10H)-one.
- E. 3-methyl-2,3-dihydro-10-(4'-fluorobenzyl)-imidazo[2,1-b]quinazolin-5(10H)-one.
- F. 10-(α-methyl-benzyl)-2,3-dihydro-2,2-dimethyl-imidazo[2,1-b]quinazolin-5(10H)-one.
- G. 10-(4'-fluorobenzyl)-2,3-dihydro-2,3-dimethyl-imidazo[2,1-b]quinazolin-5(10H)-one hydrochloride, m.p. 245°C (decomp.).
- H. 11-(4'-fluorobenzyl)-2,3,4,11-tetrahydro-3-ethyl-3-methylpyrimido[2,1-b]quinazolin-6-one.
- I. 2,8,10-trimethyl-2,3-dihydro-imidazo[2,1-b]quinazolin-5(10H)-one.
- J. 10-(4'-fluorobenzyl)-2,3-dihydro-7,8-dimethoxy-2-methyl-imidazo[2,1-b]quinazolin-5(10H)-one.
- K. 10-(4'-fluorobenzyl)-2,2-dimethyl-2,3-dihydro-imidazo[2,1-b]quinazolin-5(10H)-one, m.p. 114°-118°C.
- L. 10-cyclopropylmethyl-2-methyl-2,3-dihydro-imidazo[2,1-b]quinazolin-5(10H)-one, m.p. 222°-225°C.
- M. 10-phenyl-2-methyl-2,3-dihydro-imidazo[2,1-b]quinazolin-5(10H)-one, m.p. 222°-225°C.
- N. 10-cyclopropylmethyl-7,8-dimethoxy-2-methyl-2,3-dihydro-imidazo[2,1-b]quinazolin-5(10H)-one.
- O. 2,3-dimethyl-7-methoxy-10-phenyl-imidazo[2,1-b]quinazolin-5(10H)-one.
- P. 10-cyclopropyl-2,3-dimethyl-2,3-dihydro-imidazo[2,1-b]quinazolin-5(10H)-one.
- Q. 10-cyclopropylmethyl-2,2-dimethyl-2,3-dihydro-imidazo[2,1-b]quinazolin-5(10H)-one.
- R. 10-(4'-bromobenzyl)-2,2-dimethyl-2,3-dihydro-imidazo[2,1-b]quinazolin-5(10H)-one.
- S. 10-(3',4'-difluorobenzyl)-2,2-dimethyl-2,3-dihydro-imidazo[2,1-b]quinazolin-5(10H)-one.
- T. 7-bromo-10-ethyl-2,3-dimethyl-2,3-dihydro-imidazo[2,1-b]quinazolin-5(10H)-one.
- U. 10-(2'-methylbenzyl)-2,2-dimethyl-2,3-dihydro-imidazo[2,1-b]quinazolin-5(10H)-one.
- V. 11-(3',4'dimethoxybenzyl)-3-methyl-3-ethyl-2,3,4,11-tetrahydro-pyrimido[2,1-b]quinazolin-6-one.

What is claimed is:

1. The method of effecting bronchodilation in animals comprising administering to an animal a bronchodilating effective amount of a compound of the formula:

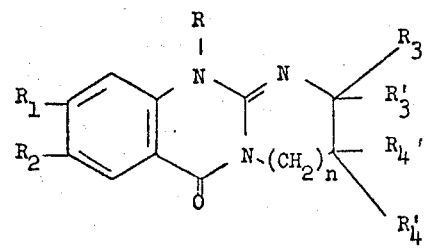

wherein each of $R_1$ and $R_2$ is, independently, hydrogen, fluoro, chloro or alkyl of 1 to 3 carbon atoms, or are either both hydroxy or both an alkoxy of 1 to 2 carbon atoms; or one is hydrogen and the other bromo, hydroxy or alkoxy of 1 to 2 carbon atoms;

$n$ is 0 or 1, each of $R_3$, $R_3'$, $R_4$ and $R_4'$ is hydrogen or alkyl of 1 to 3 carbon atoms provided that at least one but not more than three of $R_3$, $R_3'$, $R_4$ and $R_4'$ is alkyl, R is alkyl of 1 to 5 carbon atoms,

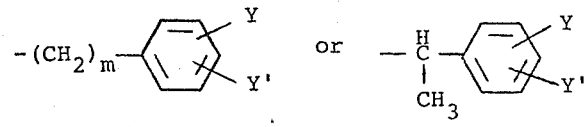

$m$ is 1 or 2, and each of Y and Y' is, independently, hydrogen, fluoro, chloro or alkyl of 1 to 3 carbon atoms, or either both are hydroxy or both alkoxy of 1 to 2 carbon atoms; or one is hydrogen and the other bromo, hydroxy or alkoxy of 1 or 2 carbon atoms, provided that no more than two of $R_1$, $R_2$, Y and Y' are hydroxy, further provided that neither of $R_1$ and $R_2$ is hydroxy when either of Y and Y' is alkoxy and further provided that neither of Y and Y' is hydroxy when either of $R_1$ and $R_2$ is alkoxy, or a pharmaceutically acceptable acid addition salt thereof.

2. The method of claim 1 in which R is

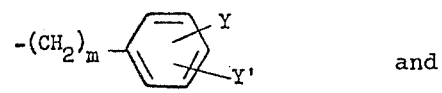 and in which $m$ is 1 or 2.

3. The method of claim 2 in which $m$ is 1.

4. The method of claim 3 in which $n$ is 0.

5. The method of claim 4 in which the compound is 2-methyl-2,3-dihydro-10-benzyl-imidazo[2,1-b]quinazolin-5(10H)-one.

6. The method of claim 5 in which the compound is in the free base form.

7. The method of claim 4 in which the compound is 2-methyl-2,3-dihydro-10-(4'-fluorobenzyl)-imidazo[2,1-b]quinazolin-5(10H)-one.

8. The method of claim 4 in which the compound is 2,3-dimethyl-2,3-dihydro-10-benzyl-imidazo[2,1-b]quinazolin-5(10H)-one.

9. The method of claim 2 in which Y' is hydrogen and Y is selected from the group consisting of hydrogen, fluoro, chloro or bromo.

10. A pharmaceutical composition comprising an inert pharmaceutically acceptable carrier and a bronchodilating effective amount of a compound of the formula

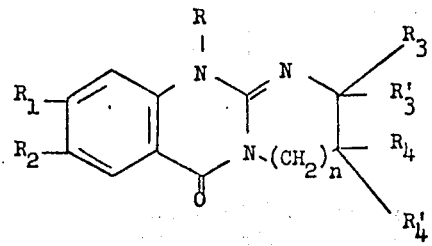

wherein each of $R_1$ and $R_2$ is, independently, hydrogen, fluoro, chloro or alkyl of 1 to 3 carbon atoms, or are either both hydroxy or both an alkoxy of 1 to 2 carbon atoms; or one is hydrogen and the other bromo, hydroxy or alkoxy of 1 to 2 carbon atoms;

$n$ is 0 or 1, each of $R_3$, $R_3'$, $R_4$ and $R_4'$ is hydrogen or alkyl of 1 to 3 carbon atoms provided that at least one but not more than three of $R_3$, $R_3'$, $R_4$ and $R_4'$ is alkyl, R is alkyl of 1 to 5 carbon atoms,

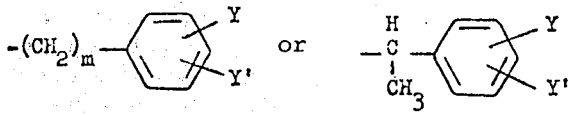

$m$ is 1 or 2, and each of Y and Y' is, independently, hydrogen, fluoro, chloro or alkyl of 1 to 3 carbon atoms, or either both are hydroxy or both alkoxy of 1 to 2 carbon atoms; or one is hydrogen and the other bromo, hydroxy or alkoxy of 1 or 2 carbon atoms, provided that no more than two of $R_1$, $R_2$, Y and Y' are hydroxy, further provided that neither of $R_1$ and $R_2$ is hydroxy when either of Y and Y' is alkoxy and further provided that neither of Y and Y' is hydroxy when either of $R_1$ and $R_2$ is alkoxy, or a pharmaceutically acceptable acid addition salt thereof.

11. A composition of claim 10 in unit dosage form and containing from 8 to 500 milligrams of the compound.

* * * * *